United States Patent
Liu (10) Patent No.: US 10,765,365 B2
(45) Date of Patent: Sep. 8, 2020

(54) SMART BRACELET

(71) Applicant: BOE TECHNOLOGY GROUP CO., LTD., Beijing (CN)

(72) Inventor: Deming Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1093 days.

(21) Appl. No.: 15/111,032

(22) PCT Filed: Nov. 11, 2015

(86) PCT No.: PCT/CN2015/094324
§ 371 (c)(1),
(2) Date: Jul. 12, 2016

(87) PCT Pub. No.: WO2016/188049
PCT Pub. Date: Dec. 1, 2016

(65) Prior Publication Data
US 2017/0105676 A1    Apr. 20, 2017

(30) Foreign Application Priority Data

May 28, 2015   (CN) .......................... 2015 1 0284802

(51) Int. Cl.
*A61B 5/00*     (2006.01)
*A61B 8/06*     (2006.01)
(Continued)

(52) U.S. Cl.
CPC ............ *A61B 5/681* (2013.01); *A44C 5/0015* (2013.01); *A44C 5/0023* (2013.01); *A61B 5/026* (2013.01);
(Continued)

(58) Field of Classification Search
CPC ..... A61B 5/681; A61B 5/684; A61B 5/02438; A61B 5/026; A61B 8/488; A61B 8/06;
(Continued)

(56) References Cited

U.S. PATENT DOCUMENTS 6,447,456 B1    9/2002  Tsubata
9,943,316 B2 *  4/2018  Kornowski ........ A61B 5/02042
(Continued)

FOREIGN PATENT DOCUMENTS

CN    203107107 U    8/2013
CN    103941873 A    7/2014
(Continued)

OTHER PUBLICATIONS

Search Report and Written Opinion dated Feb. 15, 2016 from State Intellectual Property Office of the P.R. China.
(Continued)

*Primary Examiner* — Joel Lamprecht
(74) *Attorney, Agent, or Firm* — Dilworth & Barrese, LLP.; Michael J. Musella, Esq.

(57) ABSTRACT

A smart bracelet (100) is provided. The smart bracelet (100) has a length direction, and includes: a first pulse detector (12) and a blood flow sensor (11) sequentially arranged along the length direction, wherein, the blood flow sensor (11) is configured for identifying a blood flow direction and sending a blood flow direction signal; the first pulse detector (12) is configured for detecting a pulse signal. The smart bracelet (100) can intelligently detect whether it is worn on a left hand or a right hand and avoid manually input.

19 Claims, 5 Drawing Sheets

(51) Int. Cl.
    *A61B 5/026*      (2006.01)
    *A44C 5/00*      (2006.01)
    *A61B 5/024*      (2006.01)
    *A61B 8/08*      (2006.01)

(52) U.S. Cl.
    CPC .......... *A61B 5/02438* (2013.01); *A61B 5/684* (2013.01); *A61B 8/06* (2013.01); *A61B 8/488* (2013.01); *A61B 5/0002* (2013.01); *A61B 5/489* (2013.01); *A61B 5/7445* (2013.01)

(58) Field of Classification Search
    CPC ..... A61B 5/489; A61B 5/0002; A61B 5/7445; A44C 5/0023; A44C 5/0015
    See application file for complete search history.

(56) References Cited

U.S. PATENT DOCUMENTS

| | | |
|---|---|---|
| 2005/0096557 A1 | 5/2005 | Vosburgh et al. |
| 2014/0221848 A1 | 8/2014 | Nagasaka |
| 2016/0022157 A1* | 1/2016 | Melker .............. A61B 5/02108 600/407 |
| 2016/0073914 A1* | 3/2016 | Lapetina .............. A61B 5/6824 600/384 |
| 2017/0011210 A1* | 1/2017 | Cheong ................ A61B 5/0022 |
| 2017/0049364 A1* | 2/2017 | Xu ........................ A61B 5/681 |

FOREIGN PATENT DOCUMENTS

| | | |
|---|---|---|
| CN | 104424029 A | 3/2015 |
| CN | 104615239 A | 5/2015 |
| CN | 104814726 A | 8/2015 |
| CN | 204671125 U | 9/2015 |
| WO | 2014027347 A1 | 2/2014 |
| WO | 2014168718 A1 | 10/2014 |

OTHER PUBLICATIONS

Extended European Search Report issued by the European Patent Office for the corresponding European Patent Application No. 15876396.1 dated Feb. 4, 2019.

* cited by examiner

SMART BRACELET

The present application claims priority of Chinese Patent Application No, 201510284802.4 filed on May 28, 2015, the disclosure of which is incorporated herein by reference in its entirety as part of the present application.

TECHNICAL FIELD

Embodiments of the present disclosure relate to a smart bracelet.

BACKGROUND

The smart bracelet is a wearable smart device. Through the band, users can record real-time data about exercise, sleep, and diet in daily life and synchronize these data with mobile phones, which plays a role of guiding a healthy life with the data.

Since health monitoring conditions are different when the smart bracelet is worn on a left hand and a right hand of a human body, in order to realize a better health monitoring, for example, consumers enter the wearing condition manually in a related art. However, such a manual input method is complicated, and most consumers who do not care about the specific wearing condition, such that monitoring is inaccurate and user experience is lowered.

SUMMARY

An embodiment of the present disclosure provides a smart bracelet, having a length direction, comprising: a first pulse detector and a blood flow sensor sequentially arranged along the length direction, wherein, the blood flow sensor is configured for identifying a blood flow direction and sending a blood flow direction signal; the first pulse detector is configured for detecting a pulse signal.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

DETAILED DESCRIPTION

The technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Figure 1A:
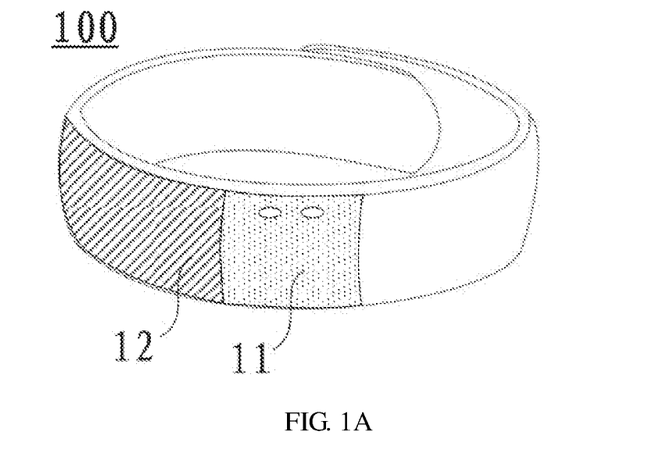
FIG. 1A is a schematic diagram of a smart bracelet provided by an embodiment of the disclosure.
Figure 1B:
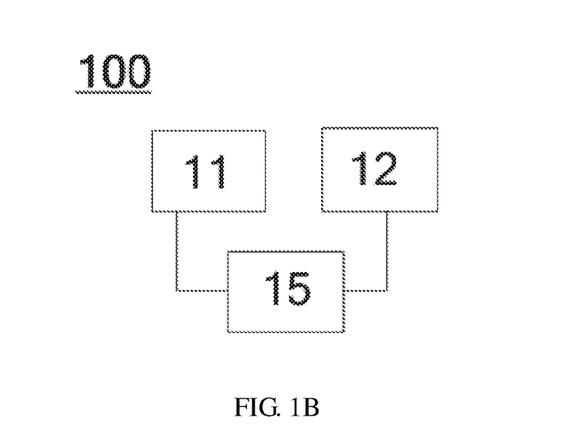
FIG. 1B is a block diagram of the smart bracelet provided by an embodiment of the disclosure.

An embodiment of the present disclosure provides a smart bracelet 100, capable of intelligently detecting whether it is worn on a left hand or a right hand and avoid manual input. As shown in FIG. 1A and FIG. 1B, the smart bracelet 100 comprises: a first pulse detector 12, a blood flow sensor 11, and a processor 15 (not shown in FIG. 1A). The smart bracelet 100 has a length direction. In a case where the smart bracelet 100 is a ring, for example, referring to FIG. 1A, its length direction is a circumferential direction. In the case where the smart bracelet 100 is straight, its length direction is a straight line direction. Along the length direction of the smart bracelet 100, the first pulse detector 12 and the blood flow sensor 11 are arranged in sequence. In the case where the smart bracelet 100 is a ring, as shown in FIG. 1A, the first pulse detector 12 is located on a side of the blood flow sensor along a bending direction of the smart bracelet; herein, "the bending direction of the smart bracelet", for example, refers to the circumferential direction of the ring-shaped smart bracelet; the expression that "the first pulse detector 12 is located on a side of the blood flow sensor along the bending direction of the smart bracelet", for example, refers to that the first pulse detector 12 is located in upstream of the blood flow sensor 11 in the circumferential direction of the ring-shaped smart bracelet. The processor 15 is communicatively connected with the first pulse detector 12 and the blood flow sensor 11. Herein, the processor can be disposed inside of the smart bracelet 100. In this case, the processor 15 can be electrically and physically connected with the first pulse detector 12 and the blood flow sensor 11. In another embodiment, the processor 15 also may not be comprised in the smart bracelet 100, and it can be, for example, comprised inside of a terminal that is communicatively connected with the smart bracelet 100.

Referring to FIG. 1A and FIG. 1B, the blood flow sensor 11 is configured for identifying a blood flow direction and sending a blood flow direction signal to the processor 15.

The first pulse detector 12 is configured for detecting a pulse signal.

The processor 15 is configured for determining whether the smart bracelet is worn on a left hand or a right hand of a human body according to the received blood flow direction signal and whether or not the first pulse detector 12 detects a pulse signal.

It should be noted that, in ultrasound imaging systems, Doppler Effect is widely applied in blood flow detecting. The principle is: ultrasonic transducer transmitting ultrasonic into the human body and receiving ultrasonic echo returned from the human body; because moving red blood cells in the blood vessels have a scattering effect on ultrasonic, which leads to ultrasonic echo frequency deviation, and the amount of the frequency deviation being related with the center frequency that transmits ultrasonic and the moving speed of red blood cells, and thus, as long as ultrasonic echo frequency deviation is measured, movements of red blood cells can be known by calculation, so as to extract blood flow state in the blood vessel. In the embodiments and the drawings of the disclosure, the blood flow sensor being a Doppler blood flow sensor is taken as an example to illustrate in details. The blood flow sensor has a transmitting terminal E and a receiving terminal R.

Figure 2A:
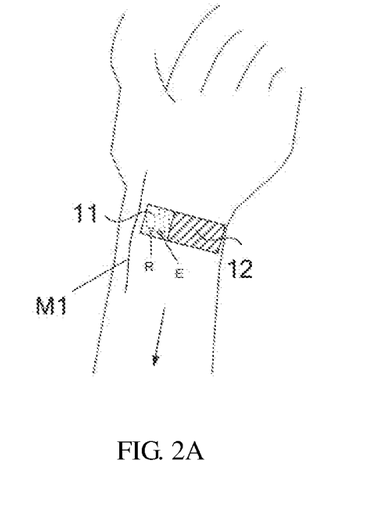
FIG. 2A and FIG. 2B are schematic diagrams showing that the smart bracelet in FIG. 1A is worn on a left hand.
Figure 2B:
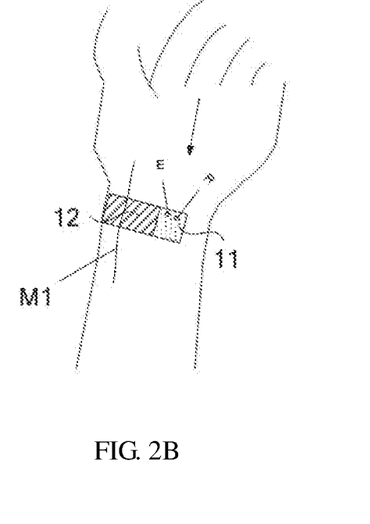

It should be noted that, because the human pulse can only be detected at a position of arm near thumb which is illustrated by pulse lines as an example in FIG. 2A and FIG. 2B. In addition, blood flow directions of artery and vein in human body are opposite, and the embodiment of the disclosure will take the blood flow direction of vein being a monitored object as an example to illustrate in detail, wherein, the blood flow direction of vein is from finger to arm.

For example, as shown in FIG. 2A and FIG. 2B, the smart bracelet can be worn on a left hand in two wearing ways of FIG. 2A and FIG. 2B. In FIG. 2A, the first pulse detector 12 cannot detect a pulse, and meanwhile, the blood flow direction signal detected by the blood flow sensor 11 is the direction away from the smart bracelet (as the arrow shown in FIG. 2A). In FIG. 2B, the first pulse detector 12 detects a pulse (here, the first pulse detector 12 is located on the left-hand overlapping position which overlaps with a left-hand pulse line M1), and meanwhile, the blood flow direction signal detected by the blood flow sensor 11 is the direction that flows to the smart bracelet (as the arrow shown in FIG. 2B). That is, if the pulse signal and the blood flow direction signal received by the processor 15 meet the above two conditions, it can be determined that the smart bracelet is worn on a left hand.

Figure 3A:
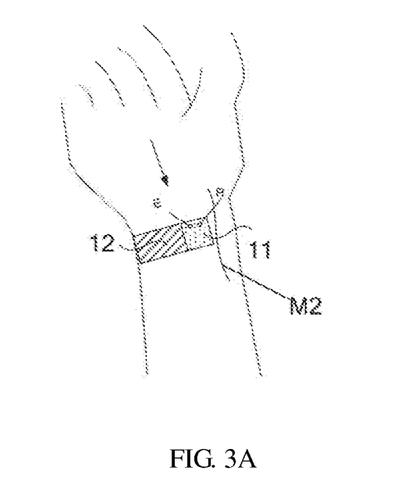
FIG. 3A and FIG. 3B are schematic diagrams showing that the smart bracelet in FIG. 1A is worn on a right hand.
Figure 3B:
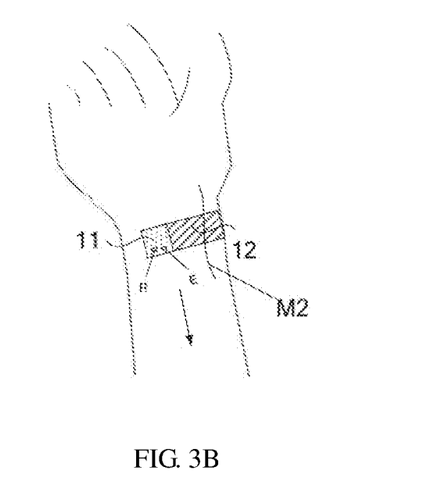

As shown in FIG. 3A and FIG. 3B, the smart bracelet can be worn on a right hand in two wearing ways of FIG. 3A and FIG. 3B. In FIG. 3A, the first pulse detector 12 cannot detect a pulse, and meanwhile, the blood flow direction signal detected by the blood flow sensor 11 is the direction that flows to the smart bracelet (as the arrow shown in FIG. 3A). In FIG. 3B, the first pulse detector 12 detects a pulse (here, the first pulse detector 12 is located on the right-hand overlapping position which overlaps with a right-hand pulse line M2), and meanwhile, the blood flow direction signal detected by the blood flow sensor 11 is the direction far away from the smart bracelet (as the arrow shown in FIG. 3B). That is, if the pulse signal and the blood flow direction signal which are received by the processor 15 meet the above two conditions, it can be determined that the smart bracelet is worn on a right hand.

In the smart bracelet provided by the embodiment of the disclosure, the first pulse detector is configured for detecting a pulse signal, the blood flow sensor is configured for detecting a blood flow direction, and the processor is configured for determining whether the smart bracelet is worn on a left hand or a right hand according to the blood flow direction signal detected by the blood flow sensor and whether or not the first pulse detector detects a pulse signal.

It should be noted that, in order to determine whether the smart bracelet is worn on the left hand or the right hand, the first pulse detector and the blood flow sensor of the smart bracelet provided by the embodiment of the disclosure are made to be located on an inner side of the arm for detecting, for example, referring to FIG. 2A to FIG. 3B. It should be noted that, according to sensitivity of the first pulse detector, reference standard for the first pulse detector detecting a pulse signal can be set up, so as to determine whether it detects a pulse signal.

Optionally, the first pulse detector is further configured for transmitting information that no pulse signal is detected to the processor in a case where no pulse signal is detected. In this case, the processor receives the information that no pulse signal is detected which is sent by the first pulse detector and determines whether the smart bracelet is worn on a left hand or a right hand of a human body.

Or, the first pulse detector is further configured for transmitting no information to the processor in a case where no pulse signal is detected. Therefore, the processor only receives the blood flow direction signal sent by the blood flow sensor. In a case where the processor does not receive the information transmitted by the first pulse detector, it can be regarded that the first pulse detector does not detect the pulse signal, so as to determine whether the smart bracelet is worn on a left hand or a right hand.

Figure 4A:
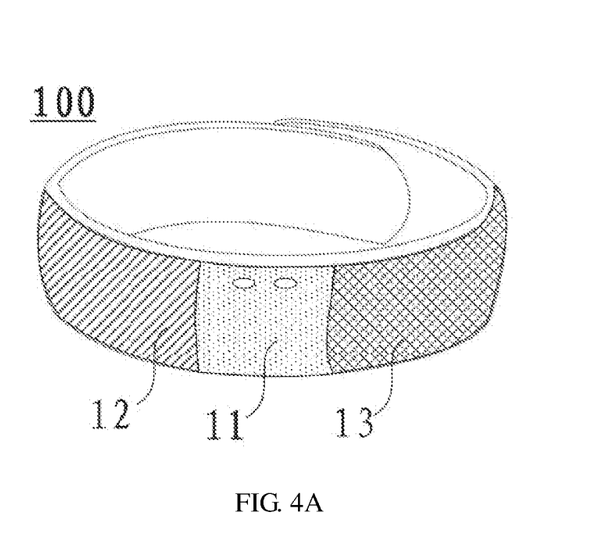
FIG. 4A is a schematic diagram of another smart bracelet provided by an embodiment of the disclosure.
Figure 4B:
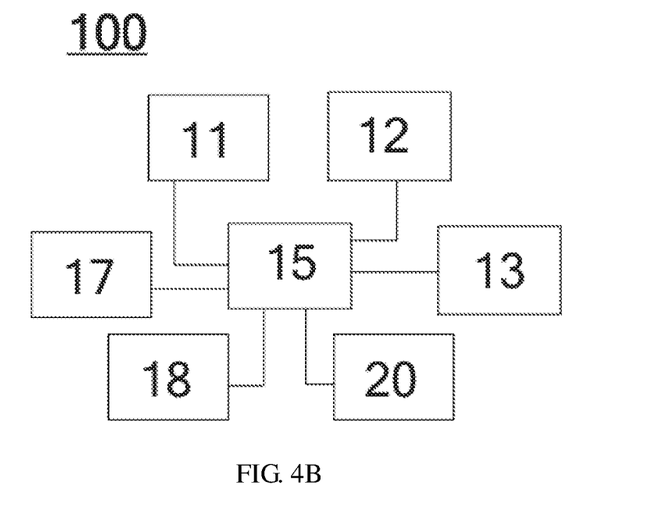
FIG. 4B is a block diagram of the smart bracelet provided by an embodiment of the disclosure.

For example, as shown in FIG. 4A and FIG. 4B, the smart bracelet 100 can further includes the second pulse detector 13. Along the length direction of the smart bracelet 100, the first pulse detector 12, the blood flow sensor 11, and the second pulse detector 13 are arranged in sequence. In a case where the smart bracelet 100 is a ring, the second pulse detector 13 is located on the other side of the blood flow sensor 11 along the bending direction of the smart bracelet; the expression that "the second pulse detector 13 is located on the other side of the blood flow sensor 11 along the bending direction of the smart bracelet", for example, refers to that the second pulse detector 13 is located in downstream of the blood flow sensor 11 in the circumferential direction of the ring-shaped smart bracelet. The second pulse detector 13 is communicatively connected with the processor 15 (not shown in FIG. 4A); the second pulse detector 13 is configured for detecting pulse signal. In a case where the processor 15 is disposed inside of the smart bracelet, the processor 15 can be electrically and physically connected with the second pulse detector 13.

The processor 15 also can be configured for determining whether the smart bracelet is worn on a left hand or a right hand of a human body according to the received blood flow direction signal and whether or not the first pulse detector 12 and the second pulse detector 13 detect a pulse signal.

In a case where the smart bracelet further comprises a second pulse detector, because the first pulse detector 12 and the second pulse detector 13 are located on both sides of the blood flow sensor 11, one of the first pulse detector and the second pulse detector detects a pulse signal when the smart bracelet is worn on a left hand or a right hand.

Figure 5A:
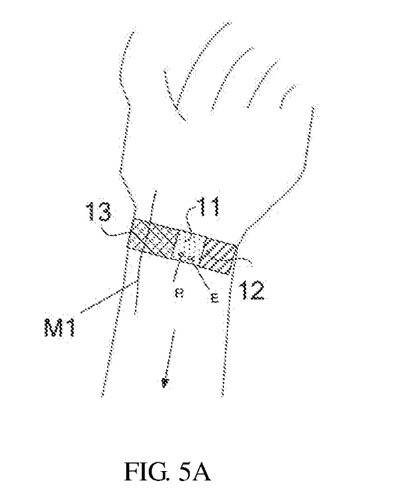
FIG. 5A and FIG. 5B are schematic diagrams showing that the smart bracelet in FIG. 4A is worn on a left hand.
Figure 5B:
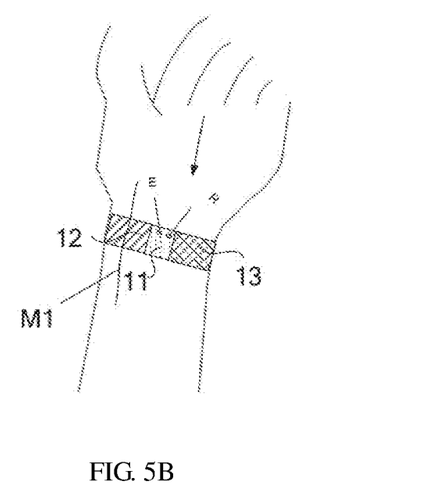

For example, as shown in FIG. 5A and FIG. 5B, the smart bracelet can be worn on a left hand in two wearing ways FIG. 5A and FIG. 5B. In FIG. 5A, the second pulse detector 13 detects a pulse (here, the second pulse detector 13 is located on the left-hand overlapping position which overlaps with a left-hand pulse line M1), and meanwhile, the blood flow direction signal detected by the blood flow sensor 11 is the direction far away from the smart bracelet (as the arrow shown in FIG. 5A). In FIG. 5B, the first pulse detector 12 detects a pulse (here, the first pulse detector 12 is located on the left-hand overlapping position which overlaps with a left-hand pulse line M1), and meanwhile, the blood flow direction signal detected by the blood flow sensor 11 is the direction that flows to the smart bracelet (as the arrow shown in FIG. 5B). That is, if the pulse signals of the first pulse detector and the second pulse detector and the blood flow direction signal which are received by the processor 15 meet the above conditions, it can be determined that the smart bracelet is worn on a left hand.

Figure 6A:
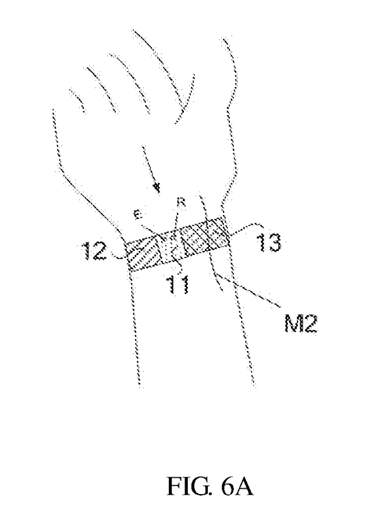
FIG. 6A and FIG. 6B are schematic diagrams showing that the smart bracelet in FIG. 4A is worn on a right hand.
Figure 6B:
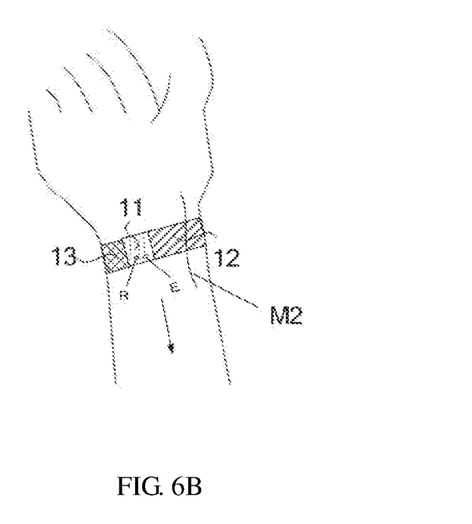

As shown in FIG. 6A and FIG. 6B, the smart bracelet can be worn on a right hand in two wearing ways of FIG. 6A and FIG. 6B. In FIG. 6A, the second pulse detector 13 detects a pulse (here, the second pulse detector 13 is located on the right-hand overlapping position which overlaps with a right-hand pulse line M2), and meanwhile, the blood flow direction signal detected by the blood flow sensor 11 is the direction that flows to the smart bracelet (as the arrow shown in FIG. 6A). In FIG. 6B, the first pulse detector 12 detects a pulse (here, the first pulse detector 12 is located on the right-hand overlapping position which overlaps with a right-hand pulse line M2), and meanwhile, the blood flow direction signal detected by the blood flow sensor 11 is the direction far away from the smart bracelet (as the arrow shown in FIG. 6B). That is, if the pulse signals of the first pulse detector and the second pulse detector and the blood flow direction signal that are received by the processor 15 meet the above conditions, it can be determined that the smart bracelet is worn on a right hand.

Optionally, the second pulse detector 13 is further configured for transmitting information that no pulse signal is detected to the processor in a case where no pulse signal is detected. Therefore, the processor receives the information that no pulse signal is detected which is transmitted by the second pulse detector and the pulse signal sent by the first pulse detector, and determines whether the smart bracelet is worn on a left hand or a right hand according to the blood flow direction.

Or, the second pulse detector is further configured for transmitting no information to the processor in a case where no pulse signal is detected. Therefore, in a case where the second pulse detector transmits no information to the processor, it is can be regarded that the second pulse detector does not detect the pulse signal.

Figure 7:
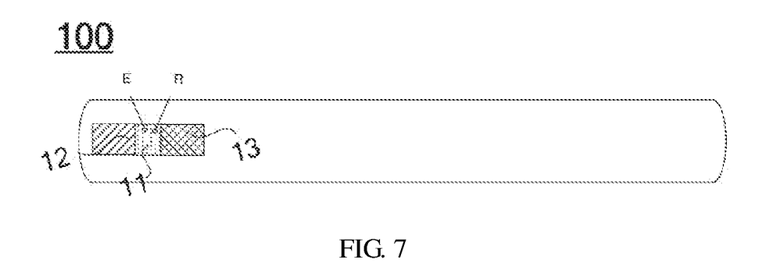
FIG. 7 is a schematic diagram of another smart bracelet provided by an embodiment of the disclosure.

For example, as shown in FIG. 7, the smart bracelet 100 can be spread out as a flat band. The blood flow sensor 11, the first pulse detector 12, and the second pulse detector 13 are located on an end of the smart bracelet in the length direction. The blood flow sensor 11, the first pulse detector 12, and the second pulse detector 13 being located on the end of the smart bracelet in the length direction is taken for example in FIG. 7. In another embodiment, the blood flow sensor, the first pulse detector, and the second pulse detector also can be located on two opposite ends of the smart bracelet in the length direction. For example, the blood flow sensor and the first pulse detector can be located on one terminal, and the second pulse detector can be located on the other terminal. The embodiment of the present disclosure only takes what is shown in FIG. 7 as an example to illustrate.

For example, referring to FIG. 4B, the smart bracelet 100 may further comprises: an information transmitter 17; the information transmitter is connected with the processor; the information transmitter is configured for receiving information that the smart bracelet is worn on the left hand or the right hand of the human body which is determined by the processor, and transmitting the information to a terminal. For example, the information transmitter can transmit information that the processor determines that the smart bracelet is worn on the left hand or the right hand of the human body to a mobile phone. The terminal judges health status of the human body according to the information that the smart bracelet is worn on a left hand or a right hand of a human body which is determined by the processor, together with other health monitoring information.

Optionally, referring to FIG. 4B, the smart bracelet 100 may further comprises: an information receiver 18; the information receiver is connected with the processor; the information receiver is configured for receiving information transmitted by the terminal, and transmitting the information to the processor. The information transmitter and the information receiver of the smart bracelet can realize the information transmission with the terminal.

For example, referring to FIG. 4B, the smart bracelet 100 may further comprises: a display screen 20; the display screen is connected with the processor 15, and configured for displaying the information determined by the processor; the determined information at least includes the information that the smart bracelet is worn on the left hand or the right hand of the human body which is determined by the processor. The determined information can further include the health status of a human body determined by the processor, and the health status can be known more conveniently through the display screen.

It is obvious for the skilled in the art that although the disclosure has been explained in detail in connection with general descriptions and specific embodiments, certain modifications or improvements can be made thereto on the basis of the present disclosure. Therefore, these modifications or improvements without departing from the spirit and scope of the present disclosure belong to the scope sought for protection in the present disclosure.

The invention claimed is:

1. A smart bracelet, having a length direction, comprising: a first pulse detector and a blood flow sensor sequentially arranged along the length direction, wherein, the blood flow sensor is configured for identifying a blood flow direction and generating and sending a blood flow direction signal, the blood flow direction is a direction away from the smart bracelet or a direction that flows to the smart bracelet; the first pulse detector is configured for detecting a pulse signal,
 the smart bracelet further comprises a processor in communicatively connection with the blood flow sensor and the first pulse detector, the processor being configured for receiving the blood flow direction signal sent by the blood flow sensor, and determining whether the smart bracelet is worn on a left hand or a right hand of a human body according to both of the received blood flow direction signal and whether or not the first pulse detector detects a pulse signal.

2. The smart bracelet according to claim 1, wherein, the first pulse detector is configured to have a left-hand overlapping position which overlaps with a left-hand pulse line in a case where the smart bracelet is worn on a left hand of a human body, and have a right-hand overlapping position which overlaps with a right-hand pulse line in a case where the smart bracelet is worn on a right hand of a human body.

3. The smart bracelet according to claim 1, wherein, the first pulse detector is further configured for transmitting information that no pulse signal is detected to the processor in a case where no pulse signal is detected;
 or,
 the first pulse detector is further configured for transmitting no information to the processor in a case where no pulse signal is detected.

4. The smart bracelet according to claim 1, further comprising: a second pulse detector, wherein, the first pulse detector, the blood flow sensor, and the second pulse detector are sequentially arranged along the length direction, and the second pulse detector is configured for detecting a pulse signal.

5. The smart bracelet according to claim 4, further comprising: a processor communicatively connected with the blood flow sensor, the first pulse detector, and the second pulse detector, the processor being configured for receiving a blood flow direction signal sent by the blood flow sensor, and determining whether the smart bracelet is worn on a left hand or a right hand of a human body according to the received blood flow direction signal and whether or not the first pulse detector and the second pulse detector detect a pulse signal.

6. The smart bracelet according to claim 4, wherein, the second pulse detector is configured to have a left-hand overlapping position which overlaps with a left-hand pulse line in a case where the smart bracelet is worn on a left hand of a human body, and have a right-hand overlapping position which overlaps with a right-hand pulse line in a case where the smart bracelet is worn on a right hand of a human body.

7. The smart bracelet according to claim 5, wherein, the second pulse detector is further configured for transmitting information that no pulse signal is detected to the processor in a case where no pulse signal is detected;

or, the second pulse detector is further configured for transmitting no information to the processor in a case where no pulse signal is detected.

8. The smart bracelet according to claim 1, wherein, the smart bracelet can be spread out as a flat band.

9. The smart bracelet according to claim 4, wherein, the blood flow sensor, the first pulse detector, and the second pulse detector are located on one end of the smart bracelet in the length direction.

10. The smart bracelet according to claim 1, wherein, the blood flow sensor is a Doppler blood flow sensor.

11. The smart bracelet according to claim 1, further comprising: an information transmitter in connection with the processor;

the information transmitter is configured for receiving information that the smart bracelet is worn on a left hand or a right hand of a human body which is determined by the processor, and transmitting the information to a terminal.

12. The smart bracelet according to claim 1, further comprising: an information receiver in connection with the processor;

the information receiver being configured for receiving information transmitted by the terminal, and transmitting the information to the processor.

13. The smart bracelet according to claim 1, further comprising: a display screen connected with the processor and configured for displaying information determined by the processor; the information at least including an information determined by the processor that the smart bracelet is worn on a left hand or a right hand of a human body.

14. The smart bracelet according to claim 1, wherein, the first pulse detector is configured to have a left-hand overlapping position which overlaps with a left-hand pulse line in a case where the smart bracelet is worn on a left hand of a human body, and have a right-hand overlapping position which overlaps with a right-hand pulse line in a case where the smart bracelet is worn on a right hand of a human body.

15. The smart bracelet according to claim 1, further comprising: a second pulse detector, wherein, the first pulse detector, the blood flow sensor, and the second pulse detector are sequentially arranged along the length direction, and the second pulse detector is configured for detecting a pulse signal.

16. The smart bracelet according to claim 2, further comprising: a second pulse detector, wherein, the first pulse detector, the blood flow sensor, and the second pulse detector are sequentially arranged along the length direction, and the second pulse detector is configured for detecting a pulse signal.

17. The smart bracelet according to claim 3, further comprising: a second pulse detector, wherein, the first pulse detector, the blood flow sensor, and the second pulse detector are sequentially arranged along the length direction, and the second pulse detector is configured for detecting a pulse signal.

18. The smart bracelet according to claim 5, wherein, the second pulse detector is configured to have a left-hand overlapping position which overlaps with a left-hand pulse line in a case where the smart bracelet is worn on a left hand of a human body, and have a right-hand overlapping position which overlaps with a right-hand pulse line in a case where the smart bracelet is worn on a right hand of a human body.

19. The smart bracelet according to claim 5, further comprising: an information transmitter in connection with the processor;

the information transmitter is configured for receiving information that the smart bracelet is worn on a left hand or a right hand of a human body which is determined by the processor, and transmitting the information to a terminal.

* * * * *